United States Patent
Miller et al.

(10) Patent No.: US 9,205,412 B2
(45) Date of Patent: Dec. 8, 2015

(54) CATALYST FOR POLYOL HYDROGENOLYSIS

(71) Applicant: Clariant Corporation, Louisville, KY (US)

(72) Inventors: Aaron B. Miller, San Ramon, CA (US); Malati Raghunath, Palo Alto, CA (US); Valery Sokolovskii, Santa Clara, CA (US); Claus G. Lugmair, San Jose, CA (US); Anthony F. Volpe, Jr., Santa Clara, CA (US); Wenqin Shen, Louisville, KY (US); Wayne Turbeville, Crestwood, KY (US)

(73) Assignee: CLARIANT CORPORATION, Louisville, KY (US)

( * ) Notice: Subject to any disclaimer, the term of this patent is extended or adjusted under 35 U.S.C. 154(b) by 158 days.

(21) Appl. No.: 13/781,829

(22) Filed: Mar. 1, 2013

(65) Prior Publication Data
US 2014/0249334 A1 Sep. 4, 2014

(51) Int. Cl.

| | | |
|---|---|---|
| *B01J 23/72* | (2006.01) | |
| *B01J 23/89* | (2006.01) | |
| *B01J 23/86* | (2006.01) | |
| *B01J 23/889* | (2006.01) | |
| *B01J 21/06* | (2006.01) | |
| *B01J 21/18* | (2006.01) | |
| *B01J 23/755* | (2006.01) | |
| *B01J 23/83* | (2006.01) | |
| *B01J 23/835* | (2006.01) | |
| *B01J 23/843* | (2006.01) | |
| *B01J 37/02* | (2006.01) | |
| *B82Y 30/00* | (2011.01) | |
| *C07C 29/00* | (2006.01) | |
| *B01J 37/18* | (2006.01) | |
| *B01J 35/02* | (2006.01) | |

(52) U.S. Cl.
CPC ............ *B01J 23/8993* (2013.01); *B01J 21/066* (2013.01); *B01J 21/18* (2013.01); *B01J 21/185* (2013.01); *B01J 23/755* (2013.01); *B01J 23/83* (2013.01); *B01J 23/835* (2013.01); *B01J 23/8435* (2013.01); *B01J 23/8437* (2013.01); *B01J 23/866* (2013.01); *B01J 23/868* (2013.01); *B01J 23/8892* (2013.01); *B01J 23/8926* (2013.01); *B01J 37/0201* (2013.01); *B82Y 30/00* (2013.01); *C07C 29/00* (2013.01); *B01J 35/023* (2013.01); *B01J 37/18* (2013.01)

(58) Field of Classification Search
CPC ........ B01J 23/72; B01J 23/755; B01J 23/866; B01J 23/868
See application file for complete search history.

(56) References Cited

U.S. PATENT DOCUMENTS

| | | |
|---|---|---|
| 4,476,331 A | 10/1984 | Dubeck et al. |
| 6,291,725 B1 | 9/2001 | Chopade et al. |
| 6,677,385 B2 | 1/2004 | Werpy et al. |
| 6,841,085 B2 | 1/2005 | Werpy et al. |
| 7,230,141 B2 | 6/2007 | Bottke et al. |
| 7,692,001 B2 | 4/2010 | Holcomb |
| 2009/0088317 A1 | 4/2009 | Frye, Jr. |
| 2010/0019191 A1 | 1/2010 | Hoffer et al. |
| 2010/0130788 A1 | 5/2010 | Coelho Tsou |
| 2011/0207972 A1 | 8/2011 | Brown |
| 2011/0301021 A1 * | 12/2011 | Liu et al. .................. 502/170 |
| 2011/0319672 A1 | 12/2011 | Liu et al. |
| 2012/0071700 A1 | 3/2012 | Huang |

FOREIGN PATENT DOCUMENTS

| | | |
|---|---|---|
| WO | 2008071616 | 6/2008 |
| WO | 2008071641 | 6/2008 |

OTHER PUBLICATIONS

Dasari, Mohanprasad, "Low-pressure hydrogenolysis of glycerol to propylene glycol," Applied Catalysis A (281) p. 225-231 (2005).
Yu, Weiqiang, "Aqueous hydrogenolysis of glycerol over NI—Ce/AC catalyst: Promoting effect of Ce on catalytic performance," Applied Catalysis A (383) p. 73-78 (2010).

* cited by examiner

*Primary Examiner* — Sudhakar Katakam

(57) ABSTRACT

Ethylene glycol and propylene glycol may be made by hydrogenolysis of a polyol comprising the steps of reacting a polyol with hydrogen in the presence of a hydrogenolysis catalyst. The hydrogenolysis comprises nickel, one or more promoter, and one or more support. The promoter is selected from bismuth, silver, tin, antimony, gold, lead, thallium, cerium, lanthanum, and manganese. The support is selected from zirconia and carbon. A zirconia support comprises a zirconia textual promoter, which is selected from Cr, Mo, W, Nb, Ce, Ca, Mg, La, Pr, Nd, Al, and P. If the support comprises carbon, then the promoter is selected from bismuth and antimony. In another embodiment, if the support comprises carbon, then both the promoter is selected from bismuth and antimony, and the catalyst comprises copper. In another embodiment, the catalyst additionally comprises copper.

17 Claims, No Drawings

CATALYST FOR POLYOL HYDROGENOLYSIS

BACKGROUND

As the chemicals industry moves away from petroleum-based materials, the efficient formation of glycols from renewable sources is a highly desirable reaction pathway. Ethylene glycol is a precursor to polyesters and polyethylene terephthalate (PET), while propylene glycol is widely used in the chemicals industry. These glycols are currently produced from petrochemicals, however they can also be derived from renewable biomass.

The concept of converting sugar alcohols to polyols, mainly ethylene glycol (EG), propylene glycol (PG), and glycerin (GLY), has been known for over seven decades. Many research papers and patents have been published on this topic. Besides the three major products, minor products include primary alcohols, such as ethanol and propanol, butandiols, even trace adols and acids. Depending on reaction conditions, gaseous products will include $CO_2$, CO, and methane. A common feature in these processes is the presence of water as a solvent.

The main obstacles to commercialization of the process include the low selectivity towards the marketable products and high production cost because of elevated operation pressure and temperature, usually over 100 bar and 200° C., and difficulties in product separation. Also, it was found that higher pH is necessary to increase the reaction rate and the product selectivity. This further worsens proper operation of heterogeneous catalyst and could result in the disintegration of supports, as well as leaching and sintering of active metals. These conditions render a great challenge to commonly available materials for supported heterogeneous catalysts.

Prior work has identified supported Ru-, Rh-, Ir-, Ni-, Re- and Pd-based materials as catalysts for glycol production from ligno-cellulosic polyols such as sorbitol and xylitol. For example, U.S. Pat. No. 6,291,725, issued Sep. 18, 2001, to Chopade et al., disclosed Ru on alumina, zirconia and carbon support; PCT Publication No. WO 2008/071616, filed on Dec. 6, 2007, by Hoffer et al., disclosed a catalyst comprising iridium on carriers selected from carbon, titanium oxide and calcium carbonate for EG, PG production from polyols. However, there have been no reports of an economically viable catalyst with sufficient selectivity to produce glycols to be widely implemented in the chemicals industry.

A method to prepare polyacid stabilized zirconia support, which is hydrothermally stable in aqueous phase hydrogenation and hydrogenolysis reactions, is described in U.S. Patent Publication No, 2011/0301021, Mar. 3, 2010, by Lui et al. The process for conversion of sugar, sugar alcohol, or glycerin to short chain glycols, EG and PG, by using the polyacid stabilized zirconia is described in U.S. Patent Publication No. 2011/0319672, filed Mar. 3, 2010, by Lui et al. The active metals, group (VIII) and group 11 and combinations thereof, were described as catalyst on the promoted zirconia support for the process, specifically, Ni, Cu, and tin-promoted Ni. U.S. Patent Publication Nos. 2011/0301021 and 2011/0319672, are incorporated by reference herein in their entirety.

It is desirable to increase the EG and PG selectivity during the hydrogenolysis of polyols.

BRIEF SUMMARY

A catalyst comprises nickel, one or more promoter, and one or more support. The promoter is selected from bismuth, silver, tin, antimony, gold, lead, thallium, cerium, lanthanum, and manganese. The support is selected from zirconia and carbon. A zirconia support comprises a zirconia textual promoter, which is selected from Cr, Mo, W, Nb, Ce, Ca, Mg, La, Pr, Nd, Al, and P. If the support comprises carbon, then the promoter is selected from bismuth and antimony. In another embodiment, if the support comprises carbon, then both the promoter is selected from bismuth and antimony, and the catalyst comprises copper. In another embodiment, the catalyst additionally comprises copper.

A method for preparing ethylene glycol and propylene glycol by hydrogenolysis of a polyol comprises the steps of reacting a polyol with hydrogen in the presence of a catalyst. The catalyst comprises nickel, one or more promoter, and one or more support. The promoter is selected from bismuth, silver, tin, antimony, gold, lead, thallium, cerium, lanthanum, and manganese. The support is selected from zirconia and carbon. A zirconia support comprises a zirconia textual promoter, which is selected from Cr, Mo, W, Nb, Ce, Ca, Mg, La, Pr, Nd, Al, and P. If the support comprises carbon, then the promoter is selected from bismuth and antimony. In another embodiment, if the support comprises carbon, then both the promoter is selected from bismuth and antimony, and the catalyst comprises copper. In another embodiment, the catalyst additionally comprises copper.

A method for making a hydrogenolysis catalyst comprises the steps of: providing a solution of nickel salt and one or more promoter salts; providing one or more supports; combining the solution with the support to form the catalyst precursor; drying and calcining the catalyst precursor. The catalyst precursor is then activated by heating it in the presence of a reducing gas atmosphere, such as hydrogen. The promoter is selected from bismuth, silver, tin, antimony, gold, lead, thallium, cerium, lanthanum, and manganese. The support is selected from zirconia and carbon. A zirconia support comprises a zirconia textual promoter, which is selected from Cr, Mo, W, Nb, Ce, Ca, Mg, La, Pr, Nd, Al, and P. If the support comprises carbon, then the promoter is selected from bismuth and antimony. In another embodiment, if the support comprises carbon, then both the promoter is selected from bismuth and antimony, and the catalyst comprises copper. In another embodiment, the catalyst additionally comprises copper.

These and other objects and advantages shall be made apparent from the accompanying drawings and the description thereof.

DETAILED DESCRIPTION

Polyols (such as xylitol, sorbitol, glycerin, and mixtures thereof) may be converted to ethylene glycol, propylene glycol, or both by using a hydrogenolysis catalyst. The polyols are treated with hydrogen in an aqueous medium and in the presence of the catalyst. The catalyst comprises a promoted nickel catalyst on a support. In one embodiment, the catalyst comprises copper. The catalyst is able to efficiently produce ethylene glycol, propylene glycol, or both with few side products.

In one embodiment, the catalyst comprises nickel, one or more promoter, and one or more support. The promoter is selected from bismuth, silver, tin, antimony, gold, lead, thallium, cerium, lanthanum, and manganese. The support is selected from zirconia and carbon. A zirconia support comprises a zirconia textual promoter, which is selected from Cr, Mo, W, Nb, Ce, Ca, Mg, La, Pr, Nd, Al, and P. If the support comprises carbon, then the promoter is selected from bismuth and antimony. In another embodiment, if the support comprises carbon, then both the promoter is selected from bismuth and antimony, and the catalyst comprises copper. In another embodiment, the catalyst additionally comprises copper.

In one embodiment, the catalyst comprises nickel, one or more promoter, and one or more support. The promoter is selected from bismuth and antimony. The support is selected from zirconia and carbon. In one embodiment, the catalyst additionally comprises copper.

In one embodiment, the catalyst comprises nickel, one or more promoter, and one or more support. The promoter is selected from bismuth, silver, tin, antimony, gold, lead, thallium, cerium, lanthanum, and manganese. The support comprises zirconia and a zirconia textual promoter. The zirconia textual promoter is selected from Cr, Mo, W, Nb, Ce, Ca, Mg, La, Pr, Nd, Al, and P. In one embodiment, the catalyst additionally comprises copper.

In one embodiment, the catalyst comprises nickel, one or more promoter, and one or more support. The promoter is selected from bismuth and antimony. The support comprises zirconia and a zirconia textual promoter. The zirconia textual promoter is selected from Cr, Mo, W, Nb, Ce, Ca, Mg, La, Pr, Nd, Al, and P. In one embodiment, the catalyst additionally comprises copper.

The promoter generally increases the catalyst activity and selectivity towards glycols, while suppressing side reactions such as methane formation. In one embodiment, the promoter is selected from bismuth, silver, tin, antimony, gold, lead, thallium, cerium, lanthanum, and manganese. In one embodiment, the promoter is selected from bismuth, antimony, and silver. In another embodiment, the promoter is selected from bismuth and antimony. The support is selected from zirconia and carbon. In one embodiment, the catalyst comprises one or more promoters from about 0.01% to about 3% of the total catalyst weight, such as from about 0.5% to about 2.3%, or 1.5% to about 2%. In one embodiment, the promoter comprises silver from about 0.1% to about 3 wt % of the total catalyst weight, such as about 0.5% to about 2.5 wt %, or 1.5% to about 2 wt %. In one embodiment, the promoter comprises Bi between about 0.01% to about 2 wt % of the total catalyst weight, such as from about 0.05% to about 1 wt %, or about 0.1% to about 0.5 wt %. In one embodiment, the promoter comprises Sb between about 0.01% to about 1.5 wt % of the total catalyst weight, such as about 0.02 to about 1 wt %, or about 0.03% to about 0.07 wt %. In one embodiment, when the support comprises carbon, the promoter is selected from bismuth and antimony.

In one embodiment, the promoter additionally comprises copper metal. In another embodiment, the promoter is selected from bismuth, antimony, and silver. In another embodiment, the promoter comprises copper metal and a metal selected from bismuth, antimony, and silver. The catalyst may comprise up to about 10% copper by weight, such as about 0.1% to about 10 wt %, about 0.2% to about 6 wt %, or about 0.3% to about 3 wt %. In one embodiment, the amount of copper is less than the amount of nickel in the catalyst. It may be less than half the amount of nickel in the catalyst by weight.

The support provides structural support for the nickel and the promoter(s). It may also affect the reactivity and selectivity of the catalyst. In one embodiment the support is zirconia, which is typically in the monoclinic phase at room temperature. The zirconia support comprises a textual promoter. The textural promoter stabilizes the tetragonal phase of zirconia and inhibits the phase transformation to the monoclinic phase. The textural promoter can improve the crush strength and the hydrothermal stability of the carrier and stabilize the surface area and pore volume of the carrier. The zirconia textual promoter may be selected from Cr, Mo, W, Nb, Ce, Ca, Mg, La, Pr, Nd, Al, and P. In another embodiment, the zirconia textual promoter is selected from Cr, Mo, W, Nb, Ce, and La. In one embodiment, the amount of zirconia textual promoter is less than 10% of the total catalyst weight. In one embodiment the zirconia to textural promoter ratio is about 2:1 to about 20:1; such as from about 4:1 to about 18:1; or from about 8:1 to about 16:1. The zirconia support may be prepared according to the methods in U.S. Patent Publication No. 2011/0301021, with at least 80-85% stabilized tetragonal phase. The zirconia support may be used as a powder, pellet, or extrudate.

The zirconia support is prepared by combining the zirconia support precursor and the textural promoter. Zirconium and the textural promoter are precipitated, dried, shaped, then calcined. The textural supporter is added to the zirconium prior to the calcinations. The extruded or other shaped support may be calcined at temperatures ranging from about 300° C. to 1000° C. for approximately 2 to 12 hours, such as from about 400° C. to 700° C. for approximately 3 to 5 hours. In one embodiment, an extruded zirconium support is calcined at about 600° C. for approximately three hours. Alternatively, an extruded zirconium support may be calcined at a ramp of 1 degree per minute (abbreviated as "deg/m" or "° C./m" or "°/min") to 600° C. and dwell for approximately 3 hours. In another embodiment, an extruded zirconium support is calcined at about 300° C. to about 1000° C., or at about 400° C. to about 700° C., or at about 500° C. to about 600° C. for approximately 2 to 12 hours. The catalyst is prepared by mixing the calcined support, which already contains the textural supporter, with Ni and a promoter, which then may be calcined a second time.

In one embodiment, surface area of the zirconia support is about 30 to about 150 $m^2/g$, as measured by nitrogen adsorption using the BET method described in J. Am. Chem. Soc. (1938) 60, pp. 309-919, which is incorporated herein in its entirety. In one embodiment, the pore volume (PV) of the zirconia support is about 0.15 mL/g to about 0.4 mL/g. In one embodiment, the crush strength of the zirconia support is at least 1 lb/mm, at least 2 lb/mm, or at least 5 lbs/mm, depending on its use. The crush strength of a catalyst or catalyst carrier may be measured using ASTM D6175-03(2008), Standard Test Method for Radial Crush Strength of Extruded Catalyst and Catalyst Carrier Particles.

In one embodiment the support is carbon. Examples of a carbon support include, but are not limited to, activated carbon and carbon nanotubes. In one embodiment, the surface area of the carbon support is about 200 to about 400 $m^2/g$, as measured by nitrogen adsorption. The large surface area facilitates excellent metal dispersion on the support surface. In one embodiment, there is a binomial pore distribution, with the most common pore diameters at about 50 Å and about 300 Å. In one embodiment, the diameter of the small pores is in the range of from about 20 Å to about 80 Å, such as from about 30 Å to about 70 Å, or about 40 Å to about 60 Å. In one embodiment, the diameter of the large pores is in the range of about 150 Å to 500 Å, such as from about 200 Å to about 400 Å, or from about 250 Å to about 350 Å.

In one embodiment, the catalyst comprises nickel from about 1% to about 40% of the total catalyst weight, such as from about 2% to about 20 wt %, from about 2% to about 14%, or about 2.5% to about 5%. A catalyst with lower loadings of Ni provides superior metal dispersion and higher product yields. In one embodiment, the catalyst comprises about 3% to about 20 wt % nickel and about 0.01 to about 3 wt % promoter by weight relative to the total catalyst weight. In another embodiment catalyst comprises about 3 to about 20 wt % nickel, up to about 5 wt % copper by weight, and about 0.01 to about 3 wt % of an additional promoter relative to the total catalyst weight. The mass of the nickel is greater than the total mass of promoter in the catalyst. The mass of nickel is also greater than the mass of copper in the catalyst. In one embodiment, the mass of nickel is greater than the total mass of promoter and copper.

In one embodiment, the catalyst is prepared by adding the nickel to the support as a concentrated dissolved nickel salt solution. The nickel salt solution may be a nickel nitrate solution. The promoter is introduced simultaneously with nickel, also as a dissolved salt, or introduced sequentially. In one embodiment, the promoter salt comprises a promoter nitrate salt. In another embodiment, the salt comprises a promoter citrate salts, such as antimony citrate. The promoter salt solution may comprise more than one promoter.

In an exemplary process, the catalyst is prepared by using an impregnation method. The amount of metals in the metal nitrate solution exceeds the carrying capacity of the support (greater than monolayer surface coverage). The support is gently agitated in the metal nitrate solution for about 30-60 minutes. In one embodiment, for a nickel-bismuth or nickel-copper-bismuth catalyst on CrZr support, the weight ratio in the metal nitrate solution of nickel to bismuth is about 5.0 to about 0.3. Copper may optionally be added in amounts slightly greater than bismuth (nickel to copper is about 5.0 to about 0.5 by weight).

In another exemplary process, the catalyst is prepared by the incipient wetness method. The desired amount of metal precursor(s) is dissolved to form a solution which is dropped onto the catalyst support until the catalyst support is completely wetted. In other words, the volume of the added precursor solution is equal to the pore volume of the catalyst support. The process can be repeated in order to get the desired metal loading.

After the nickel and promoter(s) are added to the support, the resulting wet material is dried in an oven at about 100 to about 120° C. for 2 to 12 h and calcined at about 400 to about 600° C. for 2 to 6 h. The calcination process is optional, especially for carbon support, which should only be calcined under an inert atmosphere. The catalyst precursor may be activated by heating in a reducing gas atmosphere. The reducing gas atmosphere may be hydrogen or a mixture of gasses, such as forming gas ($H_2$ and $N_2$). The heating temperature may be from about 400° C. to about 550° C. In the activated catalyst the nickel and promoter elements may be fully or partially reduced. In one embodiment, the catalyst precursor may be activated during the hydrogenolysis reaction.

The polyol is a carbon chain with multiple alcohol functional groups. The polyol may be a straight chain or branched. The polyol may be a single polypol or a mixture of polyols. In one embodiment, the polyol is a sugar alcohol, such as a C5 or C6 sugar alcohol, such as xylitol, sorbitol, glycerin, and mixtures thereof.

The process for converting polyols to ethylene glycol propylene glycol, or both may be performed either in a batch or fixed-bed reactor. In one embodiment, in the batch reactor, the catalyst, a base, and a de-gassed polyol feed solution, are mixed at room temperature. The reactor is pressurized with hydrogen while agitating and heated to the reaction temperature. In one embodiment, the reaction temperature is about 150° C. to about 350° C., such as about 200° C. to about 250° C., about 190° C. to about 250° C., or about 190° C. to about 220° C. In one embodiment, the hydrogen pressure is about 50 to about 200 bar, such as about 60 to about 150 bar, about 65 to about 120, or about 70 to about 120 bar. Higher hydrogen pressures results in higher EG and PG selectivity and less $CO_2$ in gas phase resulting from the steam reforming reaction.

The feed for a batch or fixed-bed reactor consists of a polyol, such as xylitol in water (up to 50 wt %) and a base, such as NaOH. The molar ratio of polyol to base is between about 3:1 to about 50:1, such as about 5:1 to about 25:1, or about 5:1 to about 15:1. The base acts as a co-catalyst to increase the glycol yield. The base can be an alkoxide, hydroxide or oxide of calcium or sodium or potassium. In one embodiment, the reaction time is about 4 hours or less. If the reaction is carried out for too long, the selectivity to the desired products may be lowered. In one embodiment, the reaction takes place at about 210° C., with a feed consisting of about 25 wt % xylitol and a molar ratio of xylitol:NaOH between 10 and 12.

In one embodiment, in the fixed-bed reactor, the catalyst or catalyst precursor is loaded and activated in a flow of hydrogen in-situ before the reaction. The catalyst bed is then pressurized to the reaction pressure and then heated to the reaction temperature. In one embodiment, the reaction temperature is about 180° C. to about 350° C., such as about 200° C. to about 250° C., about 190° C. to about 250° C., or about 190° C. to about 240° C. In one embodiment, the hydrogen pressure is about 50 to about 230 bar, such as about 60 to about 200 bar, about 65 to about 150, or about 70 to about 150 bar.

Two liquid streams are introduced and pre-mixed at the entrance of the bed: one is an aqueous feed containing mainly polyol, such as xylitol (up to 50 wt %), while the other is aqueous base solution, such as sodium hydroxide. The combined stream is fed into the reactor at a liquid hourly space velocity (LHSV) of from about 0.2 to $4.0\,h^{-1}$. In one embodiment, the reaction takes place at from about 190° C. to about 240° C. and from about 80 to about 120 bar $H_2$ at LHSV between about 0.5 and about $3.0\,h^{-1}$, with a pre-mixed feed consisting of about 15 to about 25 wt % xylitol and a starting pH of from about 11.5 to about 12.0 at reaction conditions.

Glycol selectivity is calculated on a carbon basis, such that the total selectivity for all products sums to 100% For example:

$$S_{EG} = \frac{\text{mol. of } EG \times 2}{\text{mol. of polyols consumed} \times \text{total Carbon number}}$$

$$S_{PG} = \frac{\text{mol. of } PG \times 3}{\text{mol. of polyols consumed} \times \text{total Carbon number}}$$

The theoretically maximum carbon selectivity for EG is 40% and the maximum carbon selectivity for PG is 60% for xylitol hydrogenolysis if xylitol is selectively cleaved between C2 and C3. In one embodiment, the hydrogenolysis of xylitol results in an ethylene glycol (EG) selectivity of 22% or greater. In one embodiment, the hydrogenolysis of xylitol results in propylene glycol selectivity of 45% or greater.

While the present disclosure has illustrated by description several embodiments and while the illustrative embodiments have been described in considerable detail, it is not the intention of the applicant to restrict or in any way limit the scope of the appended claims to such detail. Additional advantages and modifications may readily appear to those skilled in the art.

EXAMPLES

Example 1

Nickel-Copper-Bismuth Catalyst on Cr-Promoted Zirconia Support by Impregnation Method CrZr-oxide extrudates (1 g of 0.8 mm diameter) was submerged in 3 mL of a solution of 2 M $HNO_3$ containing 75 mg/mL nickel. (from nickel nitrate), 7.5 mg/mL copper (from copper nitrate), and 4.5 mg/mL bismuth (from bismuth nitrate). The solution was gently agitated and held at 60° C. for a period of 1 hour, after which the remaining solution was decanted. The catalyst was then dried at 120° C. for 2 hours and calcined in air at 450° C. for 2 hours. Prior to introduction of the xylitol feed solution, the catalyst was heated to 450° C. in 300 sccm of forming gas (5% $H_2$/balance $N_2$), and reduced at this temperature for 8 hours.

Example 2

Nickel-Copper-Bismuth Catalyst on Cr-Promoted Zirconia Support by Incipient Wetness Method A mixed metal nitrate solution (0.35 mL) of was prepared containing 150 mg/mL nickel (from nickel nitrate), 30 mg/mL copper (from copper nitrate), and 6 mg/mL bismuth (from bismuth nitrate). The mixed metal nitrate solution was added drop-wise to 1 g of 0.8 mm diameter CrZr-oxide extrudates, and the wetted extrudates were vortexed vigorously for 1 minute. The catalyst was then dried at 120° C. for 2 hours and calcined in air at 450° C. for 2 hours. Prior to introduction of the xylitol feed solution, the catalyst was heated to 450° C. in 300 sccm of forming gas (5% $H_2$/balance $N_2$), and reduced at this temperature for 8 hours.

Example 3

Nickel-Antimony Catalyst on Cr-Promoted Zirconia Support by Impregnation Method

CrZr-oxide extrudates (1 g of 0.8 mm diameter) was submerged in 3 mL of an aqueous solution containing 75 mg/mL nickel (from nickel nitrate) and 0.75 mg/mL antimony from antimony citrate). The solution was gently agitated and held at 60° C. for a period of 1 hour, after which the remaining solution was decanted. The catalyst was then dried at 120° C. for 2 hours and calcined in air at 450° C. for 2 hours. Prior to introduction of the xylitol feed solution, the catalyst was heated to 450° C. in 300 sccm of forming gas (5% $H_2$/balance $N_2$), and reduced at this temperature for 8 hours.

Example 4

Nickel-Copper-Silver Catalyst on Cr-Promoted Zirconia Support by Impregnation Method CrZr-oxide extrudates (1 g of 0.8 mm diameter) was submerged in 3 mL of a solution of 2 M $HNO_3$ containing 75 mg/mL nickel (from nickel nitrate), 7.5 mg/mL copper (from copper nitrate), and 15 mg/mL silver (from silver nitrate). The solution was gently agitated and held at 60° C. for a period of 1 hour, after which the remaining solution was decanted. The catalyst was then dried at 120° C. for 2 hours and calcined in air at 450° C. for 2 hours. Prior to introduction of the xylitol feed solution, the catalyst was heated to 450° C. in 300 sccm of forming gas (5% $H_2$/balance $N_2$), and reduced at this temperature for 8 hours.

Example 5

Nickel-Copper-Silver Catalyst on Carbon Nanotubes (CNT) Support by Incipient Wetness Impregnation A mixed metal nitrate solution of was prepared containing 150 mg/mL nickel (from nickel nitrate), 30 mg/mL copper (from copper nitrate), and 45 mg/mL silver (from silver nitrate). The mixed metal nitrate solution (0.3 mL) was added drop-wise to 0.3 g of 1.6 mm diameter CNT extrudates (Hyperion), and the wetted extrudates were vortexed vigorously for 1 minute. The catalyst was then dried at 120° C. for 2 hours. Prior to introduction of the xylitol feed solution, the catalyst was heated to 450° C. in 300 sccm of forming gas (5% $H_2$/balance $N_2$), and reduced at this temperature for 8 hours.

Example 6

The above mentioned examples were scaled up to prepare 50 g of each catalyst for fixed bed testing purpose. Before reaction, the catalyst was activated in-situ at 450° C. for 4 h with a heating ramping rate of 5° C./min in a hydrogen flow with gas hour space velocity (GHSV) of 1000 $h^{-1}$

Example 7

Hydrogenolysis of Xylitol in a Batch Micro-Reactor by Ni—Cu—Bi/CrZr Catalyst

A reduced Ni—Cu—Bi/CrZr catalyst (0.2 g) was combined in a batch reactor with 1.8 mL of a de-gassed aqueous feed solution containing 25 wt % xylitol and a 12:1 molar ratio of xylitol:NaOH. The reactor was pressurized with $H_2$ to 1015 psi (~70 bar) and heated to 210° C. while vortexing at 800 rpm. The reaction was continued for 4 hours, after which the reactor was depressurized and cooled, and products were analyzed.

The examples show higher selectivity for the desirable EG and PG products than the comparative examples. In addition, some examples have a higher xylitol conversion than the comparative examples. A secondary benefit is that the examples have the same or lower selectivity to GLY, which is a less desired product.

TABLE 1

Xylitol Hydrogenolysis in a Batch Micro-Reactor

| Metal Loading (wt %) | Support | Testing Conditions | Xylitol Conversion | EG Selectivity | PG Selectivity | GLY Selectivity |
|---|---|---|---|---|---|---|
| *Ni (4) | CrZr-oxide | 210° C., 70 bar, 4 h | 67% | 20% | 21% | 13% |
| *Ni (4) Cu (0.4) | CrZr-oxide | 210° C., 70 bar, 4 h | 53% | 21% | 25% | 13% |

TABLE 1-continued

Xylitol Hydrogenolysis in a Batch Micro-Reactor

| Metal Loading (wt %) | Support | Testing Conditions | Xylitol Conversion | EG Selectivity | PG Selectivity | GLY Selectivity |
|---|---|---|---|---|---|---|
| Ni (4.2) Cu (0.3) Ag (1.7) | CrZr-oxide | 210° C., 70 bar, 4 h | 66% | 22% | 28% | 11% |
| Ni (3.4) Cu (0.3) Bi (0.3) | CrZr-oxide | 210° C., 70 bar, 4 h | 61% | 24% | 35% | 8% |
| Ni (3.5) Bi (0.3) | CrZr-oxide | 210° C., 70 bar, 4 h | 64% | 24% | 32% | 10% |
| Ni (4) Cu (0.3) Sb (0.05) | CrZr-oxide | 210° C.,70 bar, 4 h | 70% | 23% | 30% | 13% |
| Ni (4) Sb (0.05) | CrZr-oxide | 210° C., 70 bar, 4 h | 75% | 23% | 29% | 13% |
| Ni (5) Cu (1) Sn (0.2) | CrZr-oxide | 210° C., 70 bar, 4 h | 58% | 22% | 28% | 13% |
| Ni (5) Sn (0.1) | CrZr-oxide | 210° C., 70 bar, 4 h | 53% | 22% | 29% | 10% |
| *Ni (5) Cu (1) | CNT | 210° C., 70 bar, 4 h | 66% | 23% | 31% | 12% |
| *Ni (5) Re (0.5) | Activated Carbon | 210° C., 70 bar, 4 h | 54% | 20% | 22% | 10% |
| *Ni (5) Cu (1.5) Ag (2) | CNT | 210° C., 70 bar, 4 h | 67% | 24% | 31% | 11% |

EG = Ethylene Glycol;
PG = 1,2 propylene glycol;
GLY = Glycerin;
CNT = carbon nano-tube;
*comparison

Example 8

Hydrogenolysis of Xylitol in a Fixed-Bed Reactor by a Ni—Cu—Sb/CrZr Catalyst The catalyst (15 mL) was diluted in a 1 to 1 volumetric ratio using ø3 mm stainless steel (SS) balls and loaded into a fixed-bed reactor (FBR). The diluted catalyst bed was sandwiched in between two SS ball layers for supporting and for gas/liquid feed distribution. The catalyst was activated in situ before testing. The testing was conducted between 80 to 120 bar hydrogen pressure at 210° C. to 230° C. with variation of liquid hour space velocity (LHSV) from 0.8 h$^{-1}$ to 3 h$^{-1}$. The liquid feed contained 25 wt % xylitol with a xylitol:NaOH molar ratio of 10:1. The hydrogen/xylitol molar ratio was maintained at 10 through the entire test. The liquid product was sampled every 8 to 10 h during the test and analyzed by HPLC with Waters IC-PAK™ ion exclusion column. The test went through 4 testing stages with total 340 hour-on-stream (HOS) without any deactivation observed. The fixed-bed reactor testing results are summarized in table 2.

The examples show higher selectivity for the desirable EG and PG products than the comparative examples. In addition, some examples have a higher xylitol conversion than the comparative examples. A secondary benefit is that the examples have the same or lower selectivity to GLY, which is a less desired product.

TABLE 2

Xylitol Hydrogenolysis in a Fixed-bed Reactor

| Metal Loading (wt %) | Support | Testing Conditions | Total HOS | Apparent Deactivation | Xylitol Conversion | EG Selectivity | PG Selectivity | GLY Selectivity |
|---|---|---|---|---|---|---|---|---|
| *Ni (12) Cu (4) | CrZr-oxide | 210° C., 120 bar, 0.5 h$^{-1}$ | 360 | No | 97% | 25% | 45% | 4% |
| *Ni (4.2) Cu (0.3) Ag (1.7) | CrZr-oxide | 190° C., 80 bar, 0.5 h$^{-1}$ | 440 | No | 95% | 28% | 44% | 7% |
| Ni (11.7) Cu (1.0) Ag (1.3) | CNTs | 190° C., 120 bar, 0.5 h$^{-1}$ | 150 | Yes | 74% | 31% | 50% | 4% |
| Ni (3.4) Cu (0.3) Bi (0.3) | CrZr-oxide | 210° C., 100 bar, 0.8 h$^{-1}$ | 490 | No | 93% | 30% | 48% | 4% |
| Ni (3.5) Bi (0.3) | CrZr-oxide | 210° C., 100 bar, 0.8 h$^{-1}$ | 490 | No | 95% | 29% | 47% | 4% |
| Ni (2.3) Cu (0.1) Sb (0.2) | CrZr-oxide | 210° C., 120 bar, 1 h$^{-1}$ | 340 | No | 98% | 30% | 49% | 4% |

TABLE 2-continued

Xylitol Hydrogenolysis in a Fixed-bed Reactor

| Metal Loading (wt %) | Support | Testing Conditions | Total HOS | Apparent Deactivation | Xylitol Conversion | EG Selectivity | PG Selectivity | GLY Selectivity |
|---|---|---|---|---|---|---|---|---|
| Ni (2.4) Sb (0.2) | CrZr-oxide | 210° C., 120 bar, 1 h$^{-1}$ | 340 | No | 98% | 29% | 47% | 4% |
| *Ni (40) | Al$_2$O$_3$ | 200° C., 80 bar, 3 h$^{-1}$ | 250 | No | 93% | 26% | 35% | 11% |

EG = ethylene glycol;
PG = 1,2-propylene glycol;
GLY = glycerin;
*comparison

Example 9

Glycerin Hydrogenolysis in a Fixed Bed Reactor Over Ni—Cu—Sb/CrZr and Ni—Sb/CrZr The Sb promoted NiCu and Ni catalysts on ZrCr were studied for glycerin hydrogenolysis. The test was conducted after 340 HOS evaluation of xylitol hydrogenolysis by switching the feed from xylitol to glycerin. The test was conducted at 220° C. under 120 bar hydrogen pressure with LHSV of 2 h$^{-1}$, glycerin/NaOH molar ratio of 10, hydrogen/glycerin molar ratio of 10. The feed glycerin concentration was 32 wt/%. The results are summarized in Table 3.

TABLE 3

Glycerin Hydrogenolysis in a Fixed-bed Reactor.

| Metal Loading (wt %) | Support | Testing Conditions | Total HOS | Apparent Deactivation | Glycerin Conversion | EG Selectivity | PG Selectivity |
|---|---|---|---|---|---|---|---|
| Ni (2.3) Cu (0.1) Sb (0.2) | CrZr-oxide | 220° C., 120 bar, 2 h$^{-1}$ | 32 | No | 93% | 5% | 75% |
| Ni (2.4) Sb (0.05) | CrZr-oxide | 220° C., 120 bar, 2 h$^{-1}$ | 32 | No | 95% | 5% | 71% |

Example 10

This example demonstrates the durability of the scaled-up catalyst from Example 1. The Ni—Cu—Bi/ZrCr catalyst was tested in a fixed-bed reactor under the conditions listed in Example 8, and compared with a reference Ni/Al catalyst (NiSAT208) tested in similar conditions. Table 4 and table 5 list the metal content (from catalyst leaching) in the liquid product. It was seen that aluminum leached out during the test and there was no metal leaching over the Ni—Cu—Bi/CrZr catalyst. And the spent Ni—Cu—Bi/CrZr catalysts maintained mechanical and chemical integrity.

TABLE 4

Metal content in liquid product from xylitol hydrogenolysis over NiSAT208

| HOS | Al (ppm) | Ni(ppm) |
|---|---|---|
| 40 | 1 | <1 |
| 80 | 30 | <1 |
| 120 | 30 | <1 |
| 160 | 24 | <1 |
| 207 | — | <1 |
| 243 | 4 | <1 |

TABLE 5

Metal content in liquid product from xylitol hydrogenolysis over NiCuBi/CrZr

| HOS | Ni (ppm) | Cu (ppm) | Bi (ppm) | Zr (ppm) | Cr (ppm) |
|---|---|---|---|---|---|
| 29 | <1 | <1 | <1 | <1 | <1 |
| 183 | <1 | <1 | <1 | <1 | <1 |
| 290 | <1 | <1 | <1 | <1 | <1 |
| 401 | <1 | <1 | <1 | <1 | <1 |
| 480 | <1 | <1 | <1 | <1 | <1 |

What is claimed is:

1. A catalyst comprising nickel, one or more promoter, and one or more support;
   wherein the promoter is selected from bismuth, silver, and antimony;
   wherein the support is selected from zirconia and carbon;
   wherein the zirconia support comprises a zirconia textual promoter; wherein the zirconia textual promoter is selected from Cr, Mo, W, Nb, Ce, Ca, Mg, La, Pr, Nd, Al, and P
   wherein if the support is carbon, then the promoter is selected from bismuth and antimony.

2. The catalyst of claim 1, wherein the catalyst additionally comprises copper.

3. The catalyst of claim 1, wherein the zirconia textual promoter is selected from Cr, Mo, W, Nb, Ce, and La.

4. The catalyst of claim 1, wherein the support is selected from activated carbon and carbon nanotubes.

5. The catalyst of claim 1, wherein the catalyst comprises about 1 to about 40% nickel by weight and about 0.01 to about 3% promoter.

6. The catalyst of claim 2, wherein the catalyst comprises about 1 to about 40% nickel by weight, up to about 10% copper by weight, and about 0.01 to about 3% promoter.

7. A method for hydrogenolysis of a polyol comprising the steps of reacting a polyol with hydrogen in the presence of a catalyst;

wherein the catalyst comprises nickel, one or more promoter, and one or more support;

wherein the promoter is selected from bismuth, silver, and antimony;

wherein the support is selected from zirconia and carbon;

wherein the zirconia support comprises a zirconia textual promoter; wherein the zirconia textual promoter is selected from Cr, Mo, W, Nb, Ce, Ca, Mg, La, Pr, Nd, Al, and P wherein if the support is carbon, then the promoter is selected from bismuth and antimony.

8. The method of claim 7, wherein the polyol comprises a sugar alcohol selected from xylitol, sorbitol, glycerin, and mixtures thereof.

9. The method of claim 7, wherein the hydrogenolysis is performed in the presence of a base.

10. The method of claim 9, wherein the base is selected from NaOH, KOH, and CaO.

11. The method of claim 9, wherein the molar ratio of polyol to base is about 5:1 to about 50:1.

12. The method of claim 7, wherein the hydrogenolysis is performed at a temperature of about 180° C. to about 350° C.

13. The method of claim 7, wherein the hydrogenolysis is performed at a pressure of about 50 to about 150 bar.

14. The method of claim 7, wherein the hydrogenolysis of xylitol results in an ethylene glycol selectivity of 22% or greater.

15. The method of claim 7, wherein the hydrogenolysis of xylitol results in a propylene glycol selectivity of 45% or greater.

16. A method for making a hydrogenolysis catalyst comprising:

providing a solution of a nickel salt and one or more promoter salts;

providing one or more support;

combining the solution with the support to form the catalyst precursor;

drying the catalyst precursor;

heating the catalyst precursor in the presence of a reducing gas atmosphere;

wherein the promoter is selected from bismuth, silver, and antimony;

wherein the support is selected from zirconia and carbon;

wherein the zirconia support comprises a zirconia textual promoter; wherein the zirconia textual promoter is selected from Cr, Mo, W, Nb, Ce, Ca, Mg, La, Pr, Nd, Al, and P wherein if the support is carbon, then the promoter is selected from bismuth and antimony.

17. The method of claim 16, wherein the catalyst additionally comprises copper.

* * * * *